United States Patent
Fox

(12) 
(10) Patent No.: US 6,238,719 B1
(45) Date of Patent: May 29, 2001

(54) HIGH VISCOSITY CEREAL AND FOOD INGREDIENT FROM VISCOUS BARLEY GRAIN

(75) Inventor: Gregory J Fox, Fargo, ND (US)

(73) Assignee: Barkley Seed, Inc., Yuma, AZ (US)

( * ) Notice: Subject to any disclaimer, the term of this patent is extended or adjusted under 35 U.S.C. 154(b) by 0 days.

(21) Appl. No.: 09/485,860
(22) PCT Filed: Aug. 18, 1998
(86) PCT No.: PCT/US98/17053
   § 371 Date: Feb. 17, 2000
   § 102(e) Date: Feb. 17, 2000
(87) PCT Pub. No.: WO99/08546
   PCT Pub. Date: Feb. 25, 1999

Related U.S. Application Data

(60) Provisional application No. 60/056,562, filed on Aug. 19, 1997.

(51) Int. Cl.[7] ............................................. A23L 1/168
(52) U.S. Cl. .................. 426/560; 426/457; 426/461; 426/464; 426/508; 426/518; 426/618
(58) Field of Search ..................... 426/560, 457, 426/464, 506, 507, 508, 518, 458, 459, 460, 461, 462, 618

(56) References Cited

U.S. PATENT DOCUMENTS

| | | | |
|---|---|---|---|
| 5,063,078 | * 11/1991 | Foehse | 426/482 |
| 5,151,283 | * 9/1992 | Foehse | 426/559 |
| 5,360,619 | 11/1994 | Alexander . | |
| 5,391,388 | 2/1995 | Lewis et al. . | |
| 5,464,647 | * 11/1995 | Messick | 426/461 |
| 5,614,242 | 3/1997 | Fox . | |

FOREIGN PATENT DOCUMENTS

| | | |
|---|---|---|
| 0 393 870 A1 | 10/1990 | (EP) . |
| 0 606 080 A1 | 7/1994 | (EP) . |

OTHER PUBLICATIONS

MacGregor. 1993. Barley: Chemistry and Technology, American Association of Cereal Chemists, Inc., St. Paul, Minnesota, USA, p. 303–305, 355–365.*

Yoon, 1995. Evaluation of Selected Barley Cultivars and Their Fractions for beta–glucan enrichment and viscosity, Cereal Chemistry 72(2)187–190.*

Botham. 1997. Physicochemical Characterization of Barley Carbohydrates Resistant to Digestion in Human Ilesotomate. Cereal Chemistry 74(1)29–33.*

Derwent Abstract 1982–76250E.*
Derwent Abstract 1990–346957.*
Derwent Abstract 1992–190461.*

* cited by examiner

Primary Examiner—Carolyn Paden
(74) Attorney, Agent, or Firm—Rothwell, Figg, Ernst & Manbeck

(57) ABSTRACT

Disclosed are highly digestible barley flakes and kibbles which have elevated levels of long chained beta glucan fibers (1 mm to 6 mm long, 2 microns to 10 microns wide) providing these cereal foods and food ingredients with clinically active hypocholesterolaemic, immunostimulative, and atumorigenic properties; also disclosed are the methods to produce these flakes and kibbles.

18 Claims, No Drawings

HIGH VISCOSITY CEREAL AND FOOD INGREDIENT FROM VISCOUS BARLEY GRAIN

This application is the National Stage of International Application No. PCT/US98/17053, filed Aug. 18, 1998, which claims the benefit of U.S. Provisional Application No. 60/056,562, filed Aug. 19,1997.

FIELD OF INVENTION

The present invention relates to a clinically active hypocholesterolaemic, immunostimulative, atumorigenic food and/or food ingredients derived from waxy hulless and waxy hulless short awvn barley varieties, that have elevated levels of long chained beta glucan fiber, which is the active clinical ingredient in this food product.

It is well know in the cereal and nutritional arts that beta glucan (beta 1-4/beta 1-3 glucosyl pyranose polymer) reduces serum cholesterol, and regulates serum blood sugar in humans. Beta glucan occurs in quantity in only two cereals as soluble cell wall fiber, i.e. oats and barley. Two forms of barley have especially high levels of beta glucan, i.e. waxy hulless and waxy hulless short awn. The clinical activity of these beta glucans is related to the viscosity that is created in the intestines, and that this viscosity is created by hydrated beta glucan fibers that ranged from 1 to 6 mm in length and about 2 to 10 microns in diameter. The viscosity is directly related to the quantity and length of these fibers. These sticky fibers absorb cholesterol, fat, and sugars and flush them out of the body, this flushing action is the basis of the clinical functionality.

These same beta glucans, which are common as cell wall fiber in microbes have immunostimulative, and anti-tumorigenic properties. More recently it has become apparent that the cereal beta glucans have the same healing properties as the microbial forms. Additional new information strongly suggests that these same beta glucans have anti-inflammatory properties that have a healing effect on bone and joint disorders, and a flushing action of the blood, lymph, and interstitial fluids that results in anti cancer effects. The pharmacological functionality is related to the same properties as the nutritional functionality, chain length of beta glucan fibers. As beta glucan chains pass through the intestinal tract they are broken up in length and absorbed by intestinal lymph nodes, then passing to the other organ systems. As molecular length is reduced, functionality is reduced. Thus, the long chained beta glucan fibers associated with the waxy hulless and waxy hulless short awned barleys would be especially effective in this role as a nutritional pharmacological agent.

In the last 3 years the grain growing regions of the United States have been plagued by a fungal disease called scab, that grows on the surface of the seed, this will effect all seed to some extent, but the seed which are severely effected will be bleached and shrunken, and in the industry are called tombstones because of their appearance. This fungus produces toxins that are collectively called vomitoxins, because in quantities around 10 ppm they will cause pigs to become sick with one of the symptoms, vomiting. The disease is not considered to be toxic to humans, but there is some controversy about this point, because if nothing else people allergic to vomitoxin can die from anaphylactic shock in response to these vomitoxins. At the very least they can make people sick, and certainly are not healthful compounds.

The healthful beta glucans of barley and especially waxy hulless and waxy hulless short awn barley (High Vee™ Barley) are concentrated in the endosperm of the grain, not the bran. This makes barley unique because in oats the beta glucans are concentrated in the bran. While the general public regards bran as healthful, this is in fact some what of a misnomer in real world practice. In fact diseases like scab grow on the surface of the grain. Also, the bran fraction contains high concentrations of phytic acid, a compound that ties up essential minerals and causes mineral deficiencies in live stock and has the potential to do the same in humans. Also, the harsh lignified fiber that occurs in the bran fraction, if taken in large quantities, can have a detrimental tearing effect on the intestinal cell walls. Thus, the benefit of the fiber associated with the bran fraction is mixed at best. In the present day climate of bran acceptance, as a health benefit, it is forgotten that the development of refined milling procedures in Northern Europe to remove bran from flour was a health measure to remove toxic fungi adhering to the moldy bran, that was inevitable in the cool moist environment of Northern Europe. In waxy hulless barley, and waxy hulless short awn barley there exists a highly effective form of fiber (long chained beta glucan) that is not associated with the potentially moldy bran. In this respect waxy hulless and waxy hulless short awn barleys are truly unique.

If one looks back to antiquity, to the beginnings of human civilization, barley grain was the base component of the first breads. Barley bread was considered the bread of life. As time went on the breads wheats with strong glutinous proteins, which produced the leaven loaves became the preferred bread of the affluent. However, even as these fluffy wheat breads were being introduced, their lack of healthfulness as compared to the old heavy barley breads was noted by numerous sources. These observations continued into the 19th century AD, when high gluten strength wheat breads finally replaced the heavy barley, corn, oat, rye type breads as the bread of the people, not just the affluent. Always it was noted that the raised wheat breads while fun to eat somehow seemed less healthful than the old breads, especially those with a barley base. It should be noted that the old heavy breads were quite often a combination of grain (multi grain breads). Indeed the Roman Army that conquered much of the known world marched on multi grain bread. However, of the grains in their bread, barley was the one, that in particular was thought to give strength and vigor to the soldiers. Wheat was a luxury, barley was a functional necessity.

Beer like bread comes from antiquity, and beer comes from bread, because the first beers were made from bread that was thrown in a pot of water and allowed to ferment by the action of naturally occurring air borne yeast. Since barley was the bread of antiquity, and the bread of the people, and beer was the beverage of the people, the loaf of bread that was thrown in the pot was most often made of barley. Right from the beginning (Ancient Egypt) beer was considered a health beverage. Indeed much of the barley consumed by Roman legionnaires and gladiators was in the soluble form of beer made from barley beer loaves made from partially germinated (malted) grain. Use of low alcoholic content stout beer, which contained high levels of viscous solubles as an accepted popular health tonic consumed by the entire family continued in Europe, Africa, Mid East, and America into the first half of the 20th Century. With the development of low viscosity recreational beer in the 20th Century the use of beer as a health tonic has essentially ceased for the general public in urbanized societies. Thus, the beneficial health effects of barley grain were recognized from antiquity. It was also recognized that these benefit were retained when barley was consumed in a soluble form as beer and was associated with the viscosity of the brew, when the viscosity of beers disappeared so did the perceived health benefits. Viscous beta glucan is the active ingredient in healthful barley breads and beers. An especially potent form of viscous beta glucan, long chained beta glucan derived from specially selected waxy hulless and wax hulless short awn barleys has been described by Fox in U.S. Pat. No. 5,614,242. The present invention involves high viscosity ingredients (flakes and lubbles), which can be used as cereals and food ingredients to widely extend the use of healthful long chained viscous beta glucan. Special processing techniques are employed to insure that the long chained beta glucans are preserved through processing.

Other patents have described the use of waxy barley for the production of cereal flakes, Alexander (U.S. Pat. No. 5,360,619) and Lewis et al. (U.S. Pat. No. 5,391,388) incorporated herein. Alexander describes a dry heat stabilized flake, that is used for ready to eat food products and food ingredients. Lewis, et al. describe an uncooked whole flake cereal. Only within this invention is specially selected High Vee™ waxy hulless and waxy hulless short awn barley with high levels of long chained beta glucan resulting in high levels of beta glucan viscosity, processed in such a manner with moist heat to preserve the long chained beta glucan chains, and the associated clinical (hypocholesterolaemic) functionality in a highly digestible fully cooked product.

SUMMARY OF THE INVENTION

The present invention is a high viscosity barlev flake containing high levels of clinically active long chained, viscous, beta glucan. This product can be used directly as a hot cereal lilke oatmeal or can be used as an ingredient in a wide array of cooked or baked foods.

The method for producing the high viscosity barley flake (High Vee™ Flake) includes the following steps:

1. Selecting (High Vee™) barley grain having a waxy hulless or waxy hulless short awn genotype, and beta glucan viscosity greater than 15 cps, and long chained beta glucan concentration greater than about $1.0 \times 10^5$/ml of a 5% aqueous meal suspension.
2. Pearling said barley grain in such a manner that about 10% to 20% of the seed including bran and germ layer is abraded away.
3. Conducting vomitoxin test and selecting only pearled grain that has less than 1 ppm vomitoxin.
4. Cutting (kibbling) selected grain into 1 mm 3 mm square bits (kibbles).
5. Steam cooking the kibbles for 15 to 20 minutes at 212 to 240 degrees Fahrenheit.
6. Rolling the cooked kibbles to a thickness ranging from 0.007 inches to about 0.0030 inches.
7. Drying the resultant flakes in such a manner that a moisture level below 12% is obtained with drying temperatures never exceeding 50 degrees Centigrade.

DETAILED DESCRIPTION OF THE INVENTION

In order to provide an understanding of several of the terms used in the specification and claims, the following definitions are provided:

Beta Glucan—the term beta glucan (beta 1-4/1-3 glucosyl pyranose polymer) is intended to refer to the name of a non starchy polysaccharide in which individual glucose molecules (20,000–1,000,000) are linked by beta 1-4 and beta 1-3 linkages. Beta Glucan is soluble in warm water (40–45 degrees Centigrade), cellulose is insoluble in water. Beta glucan is the main structural material in the cell walls of barley and oat grain.

Beta Glucan Chain Analysis—As used herein, the term beta glucan chain analysis is intended to refer to a microscopic test in which the actual length and concentration of beta glucan chain fiber is measured with a microscope (100×–400×).

Beta Glucan Viscosity—the term beta glucan viscosity describes the friction that is created in a solution by the presence of beta glucan chains (fibers) and is measured in cps. All beta glucan viscosities reported herein are measured on a 5% aqueous suspension of ground grain or ground grain fractions.

Centipoise Units (cps)—the term Centipoise Units or (cps) is the name of the units commonly used to measure viscosity. By definition the fundamental unit of viscosity measurement is the "Poise", which is a material requiring a sheer stress of one dyne per square centimeter to produce a sheer of one inverse second, which has a viscosity of one poise or 100 centipoise.

Chain Length—the term chain length is a measure of beta glucan fiber length in micron, millimeters, or centimeters. Such measurements can be accomplished by mounting a measured portion (1/10th of a drop) of a beta glucan solution on a calibrated slide and viewing under 100× to 400× magnification. Long beta glucan chains are 1 mm–6 mm in length and 2–10 microns in diameter.

Drying Temperatures—the term drying temperatures refers to the ambient air temperature either naturally or artificially applied to seed as it drys to ripened grain (14% to 7% moisture). Commercial driers reach temperatures exceeding 200 degrees Fahrenheit on circulating grain. The actual seed temperature depends on exposure time and moisture content of the seed when exposed to these drying temperatures.

Fully Cooked Cereal or Grain—the term fully cooked cereal or grain is a condition in which more than 90% of the starch granules have pasted rendering them digestible in the human intestine.

High Vee™ Barley—the term High Vee™ Barley is a waxy hulless or waxy hulless short awn barley with beta glucan viscosity greater than about 15 cps and long chained beta glucan concentration greater than about 1.0×10/ml of a 5% aqueous flour suspension.

High Viscosity—The term high viscosity is defined as having more than about 15 cps.

Instant Cereal Flake—the term instant cereal flake is a cereal flake, which upon addition of boiling water, and about one minute of cooling, is ready to eat.

Long Chained Beta Glucan Fibers—the term long chained beta glucan fibers describes beta glucan fibers that are about 1 mm to about 6 mm in length and about 2 to about 10 microns in diameter.

Low Viscosity—the term low viscosity is defined as having less than about 5 cps.

Pasted (Starch) Granules—the term pasted (starch) granules refers to starch granules that subsequent to heating in a water medium at temperatures between 150 degrees Fahrenheit to 212 Fahrenheit are seen under microscopic evaluation to have cracks, internal fissures, holes, ruptures, and full breaks, which renders the granules susceptible to chemical, enzymatic, and mechanical degradation. It also renders them digestible in the human intestine. Intact granules are largely indigestible.

Pearling—the term pearling refers to a form of incomplete milling in which the grain is rotated (tumbled) over an abrasive surface in order to remove a portion of the outer seed layers or hulls. Hulled grain like barley or rice are routinely pearled to remove the adhering hulls. Hulless grains like wheat corn or hulless barley can be pearled to remove the bran layer or the pericarp/aleurone seed layer, prior to grain milling, resulting in a cleaner flour with less bran.

Quick Cereal Flake—the term quick cereal flake is a cereal flake, which is added to water and boiled for 1 to 3 minutes, allowed to cool, and then eaten.

Steam cooking—the term steam cooling is the preparation of food suitable for human consumption with wet heat at atmospheric pressure 212 degrees Fahrenheit, or under pressure at boiling points above 212 degrees Fahrenheit.

Tempering—the term tempering is the addition of water to grain often above normal storage moisture in order to render the grain more malleable or otherwise suitable for milling, flaking or other forms of grain processing.

Viscosity—the term viscosity is the measure of fluid friction. A highly viscous material is one that possesses a great deal of internal friction, it will not pour or spread as easily as material of lesser viscosity.

Whole (grained) Flour—As used herein, the term whole (grained) flour describes a whole meal derived from a grain that has been ground by any number of methods.

The High Vee™ barley grain of the present invention, (described in part in U.S. Pat. No. 5,614,242, incorporated herein) can be pearled, kibbled, steam cooked, flaked, and dried to yield cereal flakes in which there is essentially no damage or breakage to the long chained beta glucan fibers contained in the endosperm cell wall, thus preserving full clinical functionality.

It was unexpected that when specially selected High Vee™ barley grain was processed by the novel methods described herein, that an easy to digest instant cereal and food ingredient was formed in which hard to digest starch granules were pasted (ruptured and converted to a digestible form), while the active clinical component, long chained beta glucan, was left intact. The product of the present invention is unique in that it contains long chained beta glucan which instant oatmeal does not, and because of the pearling step, it is far more stable (can be stored 1 year at room temperature with no rancidity). Other patents to produce flakes from waxy or waxy hulless barley have been described but none has described or achieved a fully cooked flake with long chained beta glucan concentrations greater than $1.0 \times 10^5$/ml of an aqueous flour suspension.

One preferred embodiment of this invention is a pearled, steel cut cooked, High Vee™ flake that is suitable as an quick or instant cereal and as a food ingredient to be used in bake goods as suspended flake, in cooked foods such as sauces where it also serves as a thickener, and in meats like hamburg where it serves as a meat extender, and nutritional supplement. The preferred embodiment is described below:

1. High viscosity waxy hulless or waxy hulless short awn barley with beta glucan viscosity and long chained beta glucan concentration greater than about $1.0 \times 10^5$/ml of a 5% aqueous flour suspension is selected for processing.
2. Pearling said grain in such a manner that 10 to 20% of the seed is abraded away with the more than 50% of the germ and bran (testa and pericarp) removed.
3. Vomitoxin testing conducted on the pearled grain to insure that vomitoxin levels are less than 1 ppm on a dry weight basis.
4. The pearled vomitoxin screened seed is kibbled (cut) by corrugated steel rolls in roughly square pieces that are 1 mm to 3 mm in size.
5. The kibbles are steamed or otherwise wet cooked for 15 to 20 minutes until more than 90% of the starch granules have pasted (are cracked or broken, rendering the starch digestible in the human stomach and intestines).
6. The cooked kibbles are flaked with smooth roller mills into a flake that is 0.007 to 0.016 inches in thickness.
7. The flakes are dried at a temperature that ranges from 0 to 50 degrees centigrade, with about 26 degrees Centigrade being the optimum.

Another embodiment of this invention is the production of high viscosity (High Vee™) kibbles which can be used in food products in which a grittier mouth feel is desired. One such example is hamburg in which the kibble particle size matches the meat particle size and matches the mouth feel of hamburg. In order to achieve this, the process is halted after completion of the kibbling process (step 4) and the vomitoxin screened kibbles are removed as end product.

Another embodiment of this invention is the production of high viscosity (High Vee™) cooked kibbles which can be used in the same sort of products that are described above in the second embodiment with the added benefit of a more digestible cooked kibble. In order to achieve this, the process is taken through the steam cooking of the kibbles (step 5) and then moved directly to the drying step (step 7).

Since many of the potential users of High Vee™ are middle aged to elderly persons, and many could be sufferers of cancer, heart disease, arthritis, or other ailments, a highly digestible product is desirable and will aid in the acceptance of High Vee™ flakes by the public. One surprising outcome of all 3 embodiments is that the beta glucan viscosity in the end product (kibbles, cooked kibbles, cooked flakes) increase by approximately 50% to 100% over the starting materials due in part to the fact that the pearlings remove much insoluble fiber contained in the pericarp and testa which adds nothing to the soluble beta glucan content, thus increasing the soluble long chained beta glucan content by simple dilution effect. It is also possible that the inner layers of the seed (endosperm) contain a higher concentration of long chained viscous beta glucan. It should be noted that there is no tempering step (addition of water to grain or pearled grain) in the described embodiments. This procedure is often employed prior to flaking or kibbling but hydration has the effect of reducing the length of long chained beta glucan. Unexpectedly it has been found that when using high viscosity long chained waxy hulless or waxy hulless short awn barleys at storage moisture (6% to 13.5%), that steam cooking is a sufficient preparation for flaking or kibbling.

Also unexpectedly, it was found that by steam cooking untempered bits of grain (kibbles) a fully cooked (digestible), flake was produced in which the long chained beta glucans were preserved, with the degrading cereal beta glucanases (endogenous enzymes that degrade beta glucan) inactivated. It should be noted that neither the Alexander nor Lewis et al. processes have a kibble step before flaking, and both use tempered grain as starting material; both steps are key components to the process described herein.

It was determined that select High Vee™ waxy hulless or waxy hulless short awn barley, with a clean bright appearance and vomitoxin levels no greater than 1 ppm can be used in the above described process/invention, as a whole grain, with no health problems (associated with vomitoxin), and with a one year shelf life as described in the preferred embodiment with the result that a whole grain High Vee™ cooked flake, and kibble, (cooked and uncooked) can be produced. As with the pearled High Vee™ starting material long chain beta glucan contained in the whole grain waxy hulless and waxy hulless short awn barley grain is preserved throughout the steam cooking process.

EXAMPLES

The method of this invention is illustrated below in the following examples. These examples are submitted for illustrative purposes only and are meant in no way to limit the scope of the invention.

Example 1

A sample of high beta glucan viscosity waxy hulless barley with a beta glucan viscosity of 20 cps, a concentration of long chained beta glucan that is greater than $1.0 \times 10^5$/ml of a 5% aqueous flour suspension, and a vomitoxin concentration greater than 4 ppm is selected for processing. The barley grain is pearled so that about 15% of the seed weight is abraded away. The pearled grain is sieved over a 5/64 inch round holed sieve with the overs retained and vomitoxin ppm reduced to an acceptable level of less than 1 ppm. The resultant pearled grain is steel cut in manner well known to skilled artisans to produce kibbles that are in the form of cubes that are 1 mm to 2 mm on a side. The beta glucan viscosity increased to 40 cps, with increased long chained beta glucan concentration in these kibbles. A sample of the above described kibble was blended with hamburg, 15 parts kibble to 85 parts hamburg, and prepared and cooked in the traditional manner as patties, and found to yield an extremely juicy and tasty patty with reduced animal fat content.

Example 2

A sample of high beta glucan viscosity, waxy hulless barley with a beta glucan viscosity of 33 cps, a concentration of long chained beta glucan that is greater than $1.0 \times 10^5$/ml of a 5% aqueous flour suspension, and a vomitoxin concentration greater than 6 ppm. The barley grain is pearled so that about 20% of the seed weight is abraded away. The pearled grain is sieved over a 5/64 inch round holed sieve and the overs retained and the vomitoxin ppm reduced to an acceptable level of less than 1 ppm. The resultant pearled grain is steel cut using corrugated rollers in a manner that is well known to those skilled in the art to produce kibbles that are in the form of cubes that are 1 mm to 2 mm on a side. The kibbles are steamed cooked for 15 minutes and dried at 26 degrees to a moisture concentration of 12.0%. The beta glucan viscosity of the resultant kibble was 50 cps and long chained beta glucan concentration increased. When incorporated into hamburg at concentrations from 5% to 20% the kibbled burger was found to yield an extremely juicy and tasty patty with reduced animal fat content.

Example 3

A sample of high beta glucan viscosity waxy hulless barley with a beta glucan viscosity of 17 cps, a concentration of long chained greater than $1.0 \times 10^5$/ml of a 5% aqueous flour suspension, and a vomitoxin concentration greater than 3 ppm. The barley is pearled so that about 15% of the seed weight is abraded away, said pearled grain is sieved over a 5/64 inch round holed sieve with the overs retained and vomitoxin ppm reduced to an acceptable level of less than 1 ppm. The resultant pearled grain is steel cut in a manner well known to those skilled in the art to produce kibbles that are in the form of cubes 1 mm to 2 mm on a side. The kibbles are steamed cooked for 20 minutes at 210 to 240 degrees Fahrenheit with the temperature ascending with time until more than 90% of the starch granules within the kibbles have pasted. The cooked kibbles are immediately flaked with smooth roller mills in a manner well known in the art to form flakes that are 0.007 to 0.016 inches thickness. The flakes are then immediately dried at about 26 degrees Centigrade with constant aeration. Beta glucan viscosity of the flakes resultant increases to 30 cps, and the concentration of long chained beta glucan is maintained. The resultant high viscosity flakes can be used as an instant or quick cereal flake. The distinction between instant and quick flakes is strictly based on particle size (thickness). Instant flakes are in the 0.007 to 0.010 inch range and quick flakes are in the 0.01 to 0.018 inch range. Since the flakes have alrleady been cooked as kibbles the distinction between instant and quick flakes is based solely on speed of hydration, with smaller particles (instant flakes) hydrating more rapidly than larger (quick flakes) particles. Often it is necessary to produce quick and instant flakes as separate smooth roller mill runs, setting the rollers tighter for the thinner flakes. However, in this example a range of thicknesses were produced between 0.007 inches to 0.016 inches and the two flake types were produced (separated) by sieving. The instant/quick flakes can be used not only as a hot cereal, but also as an ingredient in baked goods such as breads, coolies, and muffins. The instant/quick flakes can also be blended with meat (meat loaf), can be used in sauces as a healthful thickener (gravies, tomato sauces), and can be used in any soup as an healthful thickener.

Example 4

A sample of high beta glucan viscosity wax, hulless barley with a beta glucan viscosity of 30 cps, a concentration of long chained beta glucan greater than $1.0 \times 10^5$/ml of a 5% aqueous flour suspension, and a vomitoxin concentration no greater than 1 ppm were selected. The whole grain kernel is steel cut in a manner well known to those skilled in the art to product kibbles that are in the form of cubes 1 mm to 2 mm on a side. The kibbles are steam cooked for 20 minutes at 210 to 240 degrees Fahrenheit with the temperature ascending with time. The cooked kibbles are immediately flaked with smooth roller mills in a manner well known in the art to form flakes that are 0.007 to 0.016 in thickness. The flakes are then dried at about 26 degrees Centigrade with constant aeration, and sieved to yield instant and quick flakes. Vomitoxin testing of the flakes indicated levels of less than 1 ppm, and long chained beta glucan analysis indicated a concentration greater than $1.0 \times 10^5$/ml of an aqueous flour suspension. The instant/quick whole grain flakes can be used not only as a hot cereal but also as an ingredient in baked goods, such as breads, cookies and muffins. The instant/quick whole grain flakes can also be blended with meat (meat loaf) or used in sauces (gravies, tomato sauces) and soups as a healthful thickener.

Example 5

A sample of quick style (High Vee™) whole grain flakes described in Example 4 was added as an ingredient to preparation of Lipton Chicken Noodle soup. This compared to a sample of whole way hulless barley flakes which were flaked with just enough steam cooking (plasticizing) to form a flake of about 0.022 inches in thickness. These whole flakes were uncooked with less than 30% of the starch granules pasted. An additional comparison was made with a commercial sample of quick oat flakes.

Waxy hulless barley flakes contain no amylose (the soluble form of starch in normal starch granules). Thus, any viscosity created as these flakes are added to hot soup is due to the soluble β-glucans. Oats, the other cereal with β-glucan, does not contain wax starch and upon heating will release both amylose and β-glucan into solution. Thus, viscosity created by the oat flakes can be due to a combination of starch and β-glucan.

The viscosity created by these cereal flakes is an indication of clinical functionality. The higher the quantity and quality of the cholesterol and fat absorbing β-glucan the more viscous the resultant fortified soup will be. Viscosity created by amylose starch is degraded quickly in the small intestine by starch degrading enzymes naturally present in the saliva and has no clinical functionality.

The methods and results of this experiment are listed below. The High Vee™ Flakes are superior to the whole, uncooked barley flakes at every concentration level. They are also clearly superior to the quick oat flakes at the ¾ oz addition level. Much if not all the viscosity of the oat flakes was due to the millky colored amylose that was observed in the soup. The oats created a 'milky' mess. The whole, uncooked barley flakes were apparent as large, hard-to-digest objects in the soup. The High Vee™ flakes at the ¼ to ½ addition level were barely detectable and easily consumed and digested. The High Vee™ flakes created a smooth, appealing mouthfeel and no aftertaste—they were basically bland and undetectable to most who sampled the soup. In addition, there was no characteristic linseed smell or taste associated with grain rancidity which is remarkable since these High Vee™ whole grain flakes were 1 year old with no special storage conditions (room temperature, 26° C.).

Experiment 1
Purpose: To compare High Vee™ flakes with whole barley flakes (WBF) and quick oat flakes.
Methods Used:
Viscosity in soup
  Boiled Lipton Soup mix with 4 C water; simmered for 5 minutes
  Weighed 1 oz (28.4 g), ¾ oz (21.3 g), ½ OZ (14.2 g) and ¼ oz (7.1 g) of each sample into individual canning jars;
  Poured 1 C of soup (not noodles) into each jar (3 jars/batch of soup) and covered;
  Allowed to sit for 40 min, then cooled to 26° C. and read the viscosity**

**Viscosity measurement—liquid was poured into a 25 ml graduated cylinder and 10 cm marked. Time (in seconds) for ball to travel 10 cm is recorded. Each second of travel time is equivalent to a cps viscosity unit.

|        |              | Viscosity (sec) | | |
|--------|--------------|-----------|-----|------|
| Amount | Liquid/solid | High Vee ™ | WBF | Oats |
| 1 oz   | 8.3          | 240       | 6   | —    |
| ¾ oz   | 11.1         | 20        | 3   | 10   |
| ½ oz   | 16.7         | 15        | 3   | —    |
| ¼ oz   | 33.3         | 3         | 2   | —    |
| water  | —            | 1         | 1   | —    |

This is just one example of how High Vee™ flakes are used as a versatile food ingredient to improve the nutritional functionality of food products while maintaining good taste and textural properties resulting in products that are both good tasting and better nutritionally.

Although the foregoing invention has been described in some detail by way of illustration and example for purposes of clarity and understanding, it will be obvious that certain changes and modifications may be practiced within the scope of the invention, as limited only by the scope of the appended claims

What is claimed:

1. A method of producing high viscosity waxy hulless barley flakes with beta glucan viscosity greater than 15 Centipoise Units (cps) and a long chained beta glucan concentration greater than about $1.0 \times 10^5$/ml of a 5% aqueous flour suspension comprising:
   (a) selecting high beta glucan viscosity barley grain;
   (b) pearling said high viscosity barley grain;
   (c) kibbling said pearled high viscosity barley grain about 1 mm to about 3 mm bits;
   (d) steam cooking the said pearled high viscosity barley kibble;
   (e) flaking the said pearled high viscosity cooked barley kibble; and
   (f) drying the said pearled high viscosity cooked barley flake at a temperature below 50 degrees Celsius.

2. High viscosity waxy hulless barley flakes with beta glucan viscosity greater than 15 cps and a long chained beta glucan concentration greater than about $1.0 \times 10^5$/ml of a 5% aqueous flour suspension, produced by the method of claim 1.

3. The high viscosity barley flakes of claim 2 wherein the flakes are made from barley having a waxy hulless short awn genotype.

4. A method of producing high viscosity waxy hulless barley kibbles with beta glucan viscosity greater than 15 cps and a long chained beta glucan concentration greater than about $1.0 \times 10^5$/ml of a 5% aqueous flour suspension, the method comprising the following steps:
   (a) selecting high beta glucan viscosity barley grain;
   (b) pearling said high viscosity barley grain; and
   (c) kibbling said pearled high viscosity barley grain about 1 mm to about 3 mm bits.

5. High viscosity waxy hulless barley kibbles with beta glucan viscosity greater than 15 cps and a long chained beta glucan concentration greater than about $1.0 \times 10^5$/ml of a 5% aqueous flour suspension, produced by the method of claim 4.

6. The high viscosity barley kibble of a claim 5 wherein the kibble is made from barley having a waxy hulless short awn genotype.

7. A method of producing steam cooked high viscosity waxy hulless barley kibbles with beta glucan viscosity greater than 15 cps and a long chained beta glucan concentration greater than about $1.0 \times 10^5$/ml of 5% aqueous flour suspension, produced by a process which comprises:
   (a) selecting high beta glucan viscosity barley grain;
   (b) pearling said high viscosity barley grain;
   (c) kibbling said pearled high viscosity barley grain about 1 mm to about 3 mm bits;
   (d) steam cooking said pearled high viscosity barley kibble; and
   (e) drying said pearled high viscosity cooked barley kibble at a temperature below 50 degrees Celsius.

8. Steam cooked high viscosity waxy hulless barley kibbles with beta glucan viscosity greater than 15 cps and a long chained beta glucan concentration greater than about $1.0 \times 10^5$/ml of a 5% aqueous flour suspension, produced by the method of claim 7.

9. Steam cooked high viscosity waxy hulless barley kibble of claim 8 wherein the kibble flake is made from barley having a waxy hulless short awn genotype.

10. A method of producing whole grain high viscosity waxy hulless barley flakes with a beta glucan viscosity greater than 15 cps and a long chained beta glucan concentration greater than about $1.0 \times 10^5$/ml of a 5% aqueous flour suspension; comprising the steps of:

(a) selecting high beta glucan viscosity barley grain;

(b) kibbling said high viscosity barley grain about 1 mm to about 3 mm bits;

(c) steam cooking the said high viscosity barley kibble;

(d) flaking the said high viscosity cooked barley kibble; and (e) drying said high viscosity cooked barley flake at a temperature below 50 degrees Celsius.

11. Whole grain high viscosity waxy hulless barley flakes with beta glucan viscosity greater than 15 cps and a long chained beta glucan concentration greater than $1.0 \times 10^5$/ml of a 5% aqueous flour suspension, produced by the method of claim 10.

12. The whole grain high viscosity barley flakes of claim 11 wherein the flakes are made from barley having a waxy hulless short awn genotype.

13. A method of producing whole grain high viscosity waxy hulless barley kibbles with beta glucan viscosity greater than 15 cps and a long chained beta glucan concentration greater than about $1.0 \times 10^5$/ml of a 5% aqueous flour suspension, the method comprising the following steps:

(a) selecting high beta glucan viscosity barley grain; and (b) kibbling said high viscosity barley grain about 1 mm to about 3 mm bits.

14. Whole grain high viscosity waxy hulless barley kibbles with beta glucan viscosity greater than 15 cps and a long chained beta glucan concentration greater than about $1.0 \times 10^5$/ml of a 5% aqueous flour suspension, produced by the method of claim 13.

15. The whole grain high viscosity barley kibble of claim 14, wherein the kibble is made from barley having a waxy hulless short awn genotype.

16. A method of producing steam cooked whole grain high viscosity waxy hulless barley kibbles with a beta glucan viscosity greater than 15 cps and a long chained beta glucan concentration greater than about $1.0 \times 10^5$/ml of a 5% aqueous flour suspension, comprising:

(a) selecting high beta glucan viscosity barley grain;

(b) kibbling said high viscosity barley grain about 1 mm to about 3 mm bits;

(c) steam cooking said high viscosity barley kibble; and (d) drying said steam cooked high viscosity barley kibble at a temperature below 50 degrees Celsius.

17. Steam cooked whole grain high viscosity waxy hulless barley kibbles with beta glucan viscosity greater than 15 cps and a long chained beta glucan concentration greater than about $1.0 \times 10^5$/ml of a 5% aqueous flour suspension, produced by the method of claim 16.

18. Steam cooked whole grain high viscosity waxy hulless barley kibble of claim 17, wherein the flake is made from barley having a waxy hulless short awn genotype.

* * * * *